United States Patent [19]
Mamounas et al.

[11] Patent Number: 5,646,034
[45] Date of Patent: Jul. 8, 1997

[54] INCREASING RAAV TITER

[76] Inventors: Michael Mamounas, 871 Stevens Ave., #1306, Solana Beach, Calif. 92075; Flossie Wong-Staal, 12737 Monterey Cypress Way, San Diego, Calif. 92130; Mark Leavitt, 8460 Via Sonoma, #47, La Jolla, Calif. 92037; Mang Yu, 1525 First St., Apt. T-207, Coronado, Calif. 92118

[21] Appl. No.: 487,080

[22] Filed: Jun. 7, 1995

[51] Int. Cl.$^6$ ............... C12N 5/22; C12N 15/86
[52] U.S. Cl. ............ 435/325; 435/320.1; 435/91.4; 435/172.3
[58] Field of Search ............... 435/69.1, 172.3, 435/240.2, 320.1

[56] References Cited

U.S. PATENT DOCUMENTS 4,797,368  1/1989  Carter et al. ............ 435/320.1
5,139,941  8/1992  Muzyczka et al. .......... 435/172.3

FOREIGN PATENT DOCUMENTS 0388758    3/1990  European Pat. Off. .
WO93/24641 12/1993  WIPO .

OTHER PUBLICATIONS

Chatterjee et al. (1993) *Methods, A Companion to Methods in Enzymology* 5: 51–59.
Cotton et al. (1992) *Proc. Natl. Acad. Sci. USA* 89: 6094–6098.
Cristiano et al. (1993) *Proc. Natl. Acad. Sci* 90: 11548–11552.
Curiel (1991) *Proc. Natl. Acad. Sci. USA* 88: 8850–8854.
Curiel et al. (1992) *Hum. Gene Ther.* 3: 147–154.
Curiel et al. (1992) *Am. J. Respir. Cell Mol. Biol.* 6: 247–252.
Flotte et al. (1993) *Proc. Natl. Acad. Sci. USA* 90: 10613–10617.
Flotte et al. (1994) *Am. J. Respir. Cell Mol. Biol.* 11: 517–521.
Harris et al. (1993) *Am. J. Respir. Cell Mol. Biol.* 9: 441–447.
Hermonat et al. (1984) *Proc. Natl. Acad. Sci.* 81: 6466–6470.
Kotin (1994) *Human Gene Therapy* 5: 793–801.
Michael et al. (1993) *J. Biol. Chem.* 268(10): 6866–6869.
McLaughlin et al. (1988) *J. Virol.* 62(6): 1963–1973.
Muzyczka (1992) *Curr. Top in Microbiol. and Immunol.* 158: 97–129.
Muzyczka (1994) *J. Clin. Invest.* 94: 1351.
Podsakoff et al. (1994) *J. Virol.* 68(9): 5656–5666.
Samulski et al. (1987) *J. Virol.* 61(10): 3096–3101.
Samulski et al. (1989) *J. Virol.* 63(9): 3822–3828.
Samulski (1993) *Current Opinion in Genetic and Development* 3: 74–80.
Tratschin et al. (1985) *Mol. Cell Biol.* 5: 3251–3260.
Wagner et al. (1990) *Proc. Natl. Acad. Sci. USA* 87: 3410–3414.
Wagner et al. (1991) *Proc. Natl. Acad. Sci. USA* 88: 4255–4259.
Wagner et al. (1992) *Proc. Natl. Acac. Sci. USA* 89: 6099–6013.
West et al. (1987) *Virology* 160: 38–47.
Wu et al. (1987) *J. Biol. Chem.* 262: 4429–4432.

*Primary Examiner*—David Guzo
*Attorney, Agent, or Firm*—Townsend and Townsend and Crew LLP

[57] ABSTRACT

Methods, kits and compositions for increasing the titer of rAAV vectors are provided.

30 Claims, 2 Drawing Sheets

INCREASING RAAV TITER

Note: This Invention was made with government support.

This invention was made with government support under contract no. DAMD 17-90-C-0094, awarded by the United States Army. The government has certain rights in this invention.

BACKGROUND OF THE INVENTION

Adeno associated viruses (AAVs) require helper viruses such as adenovirus or herpes virus to achieve productive infection. In the absence of helper virus functions, AAV integrates (site-specifically) into a host cell's genome, but the integrated AAV genome has no pathogenic effect. The integration step allows the AAV genome to remain genetically intact until the host is exposed to the appropriate environmental conditions (e.g., a lytic helper virus), whereupon it re-enters the lytic life-cycle. Samulski (1993) *Current Opinion in Genetic and Development* 3:74–80 and the references cited therein provides an overview of the AAV life cycle.

AAV-based vectors are used to transduce cells with target nucleic acids, e.g., in the in vitro production of nucleic acids and peptides, and in in vivo and ex vivo gene therapy procedures. See, West et al. (1987) *Virology* 160:38–47; Carter et al. (1989) U.S. Pat. No. 4,797,368; Carter et al. WO 93/24641 (1993); Kotin (1994) *Human Gene Therapy* 5:793–801; Muzyczka (1994) *J. Clin. Invst.* 94:1351 and Samulski (supra) for an overview of AAV vectors.

Recombinant AAV vectors (rAAV vectors) deliver foreign nucleic acids to a wide range of mammalian cells (Hermonat & Muzycka (1984) *Proc Natl Acad Sci U.S.A.* 81:6466–6470; Tratschin et al. (1985) *Mol Cell Biol* 5:3251–3260), integrate into the host chromosome (McLaughlin et al. (1988) *J Virol* 62:1963–1973), and show stable expression of the transgene in cell and animal models (Flotte et al. (1993) *Proc Natl Acad Sci U.S.A.* 90:10613–10617). Moreover, unlike retroviral vectors, rAAV vectors are able to infect non-dividing cells (Podsakoff et al. (1994) *J Virol* 68:5656–66; Flotte et al. (1994) *Am. J. Respir. Cell Mol. Biol.* 11:517–521). Further advantages of rAAV vectors include the lack of an intrinsic strong promoter, thus avoiding possible activation of downstream cellular sequences, and their naked icosohedral capsid structure, which renders them stable and easy to concentrate by common laboratory techniques.

rAAV vectors are used to inhibit, e.g., viral infection, by including anti-viral transcription cassettes in the rAAV vector. For example, Chatterjee et al. (*Science*(1992), 258:1485–1488, hereinafter Chatterjee et al. 1) describe anti-sense inhibition of HIV-1 infectivity in target cells using an rAAV vector with a constitutive expression cassette expressing anti-TAR RNA. Chatterjee et al. (PCT application PCT/US91/03440 (1991), hereinafter Chatterjee et al. 2) describe rAAV vectors, including rAAV vectors which express antisense TAR sequences. Chatterjee and Wong (*Methods, A companion to Methods in Enzymology* (1993), 5:51–59) further describe rAAV vectors for the delivery of antisense RNA. Wong Staal et al. (copending U.S. application Ser. No. 08/442,061 filed May 16, 1995) describe composite rAAV vectors which block infection by a wide range of viruses, including HIV-1, HIV-2, HTLV-1 and HTLV-2.

rAAV vectors have several properties which make them preferred gene delivery systems in clinical settings. They have no known mode of pathogenesis and 80% of people in the United States are currently seropositive for AAV (Blacklow et al. (1971) *J Natl Cancer Inst* 40:319–327; Blacklow et al. (1971) *Am J Epidemiol* 94:359–366). Because rAAV vectors have little or no endogenous promoter activity, specific promoters may be used, depending on target cell type. rAAV vectors can be purified and concentrated so that multiplicities of infection exceeding 1.0 can be used in transduction experiments. This allows virtually 100% of the target cells in a culture to be transduced, eliminating the need for selection of transduced cells.

Despite the promising advantages of rAAV vectors as a tool for gene therapy, one problem in their development for clinical use has been the cumbersome and inefficient techniques available for vector production. Packaging cell lines are not available, so present practice utilizes a helper plasmid to co-transfect adenovirus infected cells with the recombinant vector, where the helper plasmid encodes functions and structural proteins which complement AAV functions and structural proteins not encoded by the rAAV vector. Typically, this results in sub-optimal vector production due to the inefficient co-transfection step (See, Muzyczka, supra, and Kotin, supra for an overview of the difficulties in using rAAV vectors). Quite surprisingly, the present invention solves these and other problems associated with the use of AAV-based vectors.

SUMMARY OF THE INVENTION

One of the principal problems with using recombinant adeno-associated virus vectors (rAAV vectors) is the difficulty in obtaining high titers of the encapsidated vector after the initial transfection into rAAV producer cells. In this invention we describe methods for transfecting cells at extremely high efficiencies with rAAV vector nucleic acids. We further show that these new techniques result in an increase in rAAV vector titer by two orders of magnitude over what is typically achieved by standard calcium phosphate transfection. The present invention provides reliable methods of generating high titers of recombinant adeno-associated virus vectors (rAAV vectors), which are useful in vitro, ex vivo and in vivo.

In one preferred class of embodiments, the present invention provides methods for producing high titers of rAAV vectors. In the first step of the methods, a recombinant encapsidatable AAV nucleic acid (a rAAV nucleic acid) and a recombinant AAV helper nucleic acid are bound to an AAV helper virus, most typically in the presence of a nucleic acid binding molecule such as a polycation (e.g., poly-1-lysine). The rAAV nucleic acid typically encodes a nucleic acid of interest, such as a gene therapeutic agent (e.g. an anti-HIV or other anti-viral therapeutic agent such as a ribozyme, antisense gene, suicide gene or transdominant gene), as well as AAV cis-sequences necessary for packaging the nucleic acid into an AAV capsid (e.g., the AAV ITR sequences). The helper nucleic acid typically encodes AAV nucleic acids and proteins necessary for encapsidation of the rAAV nucleic acid. In preferred embodiments, the helper nucleic acid does not encode sequences necessary for encapsidating itself into a viral capsid. For instance, in one embodiment, the helper nucleic acid lacks AAV ITR sequences (an example of such a nucleic acid is the plasmid AD8). Thus, in one embodiment, the rAAV nucleic acid and the helper nucleic acid are non-homologous, and no wild-type AAV virus is produced upon expression and replication of the rAAV and helper nucleic acids in a cell. The AAV helper virus is a virus which allows replication of AAV (and rAAV vectors), such as an adenovirus or herpes virus. In one embodiment, the helper virus is replication defective. Typically, where the helper virus is replication defective, the cell is infected with a replication competent helper virus, often at the time of transfection.

The bound rAAV nucleic acid-helper AAV nucleic acid-AAV helper virus construct (optionally including a nucleic acid binding molecule such as a polycation) is then contacted with a cell in the AAV helper virus host range (i.e., a cell which the AAV helper virus can infect). The cell is then cultured under conditions which permit replication and encapsidation of the rAAV nucleic acid, thereby producing an rAAV vector (i.e., the rAAV nucleic acid contained within an AAV viral capsid). The vector is then isolated using standard techniques, e.g., for use in the transduction of a mammalian cell, e.g., for in vitro peptide or nucleic acid production, or ex vivo or in vivo gene therapy procedures.

In a related class of embodiments, the rAAV nucleic acid-AAV helper nucleic acid-AAV helper virus-nucleic acid binding molecule (e.g., where the nucleic acid binding molecule is a cation such as poly-1-lysine) construct further includes an anti-cell surface receptor molecule such as a transferrin receptor ligand (e.g., transferrin, or transferrin-poly-1-lysine).

In a second class of embodiments, methods of replicating an rAAV vector through receptor mediated endocytosis are provided. In the first step of the methods, an rAAV nucleic add and an AAV helper nucleic acid are bound to a receptor-binding ligand, thereby forming an rAAV nucleic acid-AAV helper nucleic acid-receptor binding ligand complex. The receptor-binding ligand, upon binding a cell membrane-bound receptor provides for endocytosis of the receptor binding ligand and associated complex. The rAAV nucleic acid-AAV helper nucleic acid-receptor binding ligand complex is contacted to a cell, causing endocytosis of the complex. The cell is then incubated under conditions which permit replication and encapsidation of the rAAV nucleic acid, thereby creating an rAAV vector.

Typically, the ligand is an AAV helper virus such as adenovirus or herpes virus, but in some embodiments other cell surface ligands are used, such as transferrin. When non-helper virus ligands are used, the complex often includes a helper-virus in addition to the receptor ligand and the AAV nucleic acids. However, other arrangements are also provided by the present invention. For instance, in one embodiment, the ligand-nucleic acid complex is transfected into the cell during cell infection with an AAV helper virus such as adenovirus.

In one class of embodiments, methods of integrating a target nucleic acid into a cellular genome are provided. In the first step, a recombinant AAV (rAAV) nucleic acid and an AAV helper nucleic acid are bound to an AAV helper virus, producing a bound AAV helper virus, most typically in the presence of a nucleic acid binding molecule such as a polycation (e.g., poly-1-lysine). The recombinant rAAV nucleic acid typically encodes a nucleic acid of interest, such as a polypeptide, antisense gene, or ribozyme as well as AAV cis-active sequences necessary for packaging the nucleic acid into an AAV capsid (e.g., the AAV ITR sequences). The AAV helper nucleic acid typically encodes AAV nucleic acids and proteins which operate in trans to encapsidate the rAAV nucleic acid into an AAV capsid. These trans-active sequences include, e.g., the AAV replicase and capsid genes. In preferred embodiments, the helper nucleic acid does not encode sequences necessary for encapsidating the nucleic acid into a viral capsid. For instance, in one embodiment, the AAV helper nucleic acid lacks AAV ITR sequences (an example of such a nucleic acid is the plasmid AD8 described herein). Thus, in one embodiment, the rAAV nucleic acid and the AAV helper nucleic acid are non-homologous, and no wild-type AAV virus is produced upon expression and replication of the rAAV and AAV helper nucleic acids in a cell. The AAV helper virus is a virus which allows replication of AAV and rAAV, such as an adenovirus or herpes virus. In one embodiment, the helper virus is replication defective. Typically, where the helper virus is replication defective, the cell is infected with a replication competent helper virus, generally at the same time as the transfection with the rAAV and helper nucleic acids.

A cell is then contacted with the bound helper virus and cultured under conditions which permit replication and encapsidation of the rAAV nucleic acid, thereby producing an rAAV vector. The rAAV vector is then isolated and used to transduce a cell. Most typically, the cell is a human cell, but other cells, particularly other mammalian cells such as rodent and primate cells, are also contemplated. Any cell which is infected by AAV is transducible with the rAAV vector, and AAV infects an extremely broad range of mammalian cells.

The present invention also provides compositions and related kits useful, e.g., in practicing the methods of the invention. The compositions include an AAV helper virus, an rAAV nucleic acid and an AAV helper nucleic acid as described above for the methods of the invention. Typically, the compositions also include a nucleic acid binding molecule such as a polycation (e.g., poly-1-lysine). Optionally, the compositions further include transferrin (e.g., coupled to a nucleic acid bonding molecule such as a polycation), or another receptor ligand. Kits of the present invention include a composition of the present invention, typically in a container with instructional materials for the use of the compositions of the present invention, e.g., to practice the methods of the invention.

DEFINITIONS

Unless defined otherwise, all technical and scientific terms used herein have the same meaning as commonly understood by one of ordinary skill in the art to which this invention belongs. Singleton et al. (1994) *Dictionary of Microbiology and Molecular Biology*, second edition, John Wiley and Sons (New York) provides one of skill with a general dictionary of many of the terms used in this invention. Although any methods and materials similar or equivalent to those described herein can be used in the practice or testing of the present invention, the preferred methods and materials are described. For purposes of the present invention, the following terms are defined below.

An "AAV helper virus" is a virus which supplies some or all of the functions necessary for AAV (and rAAV vector) replication which are not encoded by a wild-type AAV. Typically these functions are supplied in trans by viruses such as adenovirus or herpes virus during viral replication. Thus, adenovirus and herpes virus are examples of AAV helper viruses.

An "AAV ITR sequence" refers to the sequences which comprise the palindromic terminal repeats at the 3' and 5' ends of the AAV genome. Typically, the repeats are about 150 nucleotides in length. The AAV ITR regions provide sequences for packaging the AAV provirus (i.e., the AAV genome) into the AAV viral capsid. The ITR regions also form secondary structures which act as self-primers for AAV replication. Samulski (supra) describes AAV ITR sequences and structures.

An "adenovirus ITR" refers to the 3' and 5' terminal regions of the adenovirus genome. See, e.g., Gingeras et al. (1982) *J. Biol. Chem.* 257:13475–13491.

An "antibody" is a polypeptide substantially encoded by an immunoglobulin gene or immunoglobulin genes, or fragments thereof which specifically bind and recognize an analyte (antigen). Recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. An exemplary immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain (VL) and variable heavy chain (VH) refer to these light and heavy chains respectively. Antibodies exist e.g., as intact immunoglobulins or as a number of well characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild reducing conditions to break the disulfide linkage in the hinge region, thereby converting the F(ab)'2 dimer into an Fab' monomer. The Fab' monomer is essentially an Fab with part of the hinge region (see, *Fundamental Immunology, Third Edition*, W. E. Paul, ed., Raven Press, N.Y. (1993) for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies.

A "cell surface receptor" or a "cell membrane receptor" is a cellular receptor molecule expressed on the cell's outer membrane surface. Typically, in the context of the present invention, the binding of a cell surface receptor to its cognate ligand causes endocytosis of the receptor and ligand.

"Encapsidation" refers to the general process of incorporating a viral genome into a viral capsid.

"Endocytosis" refers generally to the phenomenon of a cell ingesting material, e.g., by phagocytosis or pinocytosis. Receptor-mediated endocytosis provides an efficient means of causing a cell to ingest material which binds to a cell surface receptor. See, Wu and Wu (1987) *J. Bio. Chem.* 262:4429–4432; Wagner et al. (1990) *Proc. Natl. Acad. Sci. U.S.A.* 87:3410–3414, and EP-A1 0388 758.

"Heterologous nucleic acid sequences" are nucleic acid sequences which are not derived from a common source. For instance, in one class of embodiments, in the context of an rAAV vector nucleic acid, a heterologous nucleic acid sequence includes the AAV ITR nucleic acid regions and sequences which are not derived from AAV, such as an anti-HIV nucleic acid (see Wong Staal et al., copending application Ser. No. 08/442,061 for a description of anti-HIV agents).

"Heterologous anti-HIV nucleic acid sequences" in the context of an AAV vector refers to an anti-HIV nucleic acid which is not derived from AAV. Examples of anti-HIV nucleic acid sequences include ribozymes which cleave the HIV genome, e.g., in the U5 region, suicide genes, decoy genes, anti-sense nucleic acid, and transdominant genes. See, Wong Staal et al. copending application Ser. No. 08/245,742 for a description of anti-HIV ribozymes.

"Heterologous anti-HIV ribozyme nucleic acid sequences" in the context of an rAAV vector refers to a nucleic acid which forms a ribozyme capable of cleaving the HIV genome. Anti-HIV ribozymes are known in the art. Examples of such ribozymes are found in Wong-Staal et al., copending application Ser. No. 08/245,742; Wong-Staal et al., copending application Ser. No. 08/442,061; Ojwang et al. (1992) *Proc Natl Acad Sci U.S.A.* 89:10802–10806; Ojwang et al. (1993) *Proc Natl Acad Sci U.S.A.* 90:6340–6344; Yamada et al.(1994) *Gene Therapy* 1:39–45; Leavitt et al. (1995) *Acad Sci U.S.A.* 92:699–703; Leavitt et al. (1994) *Human Gene Therapy* 5:1151–1120; Yamada et al. (1994) *Virology* 205:121–126, and Dropulić et al. (1992) *Journal of Virology* 66(3):1432–1441.

A "human cell" is any cell which is substantially human in origin, including organismal cells, tissue culture cells, and chimeric cells with human chromosomes.

"Infection," in the context of a viral-cell interaction refers to the process wherein a virus enters the cell. A "productive infection" refers to the process wherein a virus enters the cell, is replicated, and then released from the cell (sometimes referred to as a "lytic" infection).

"Isolating the recombinant rAAV vector" refers to the process of purifying the encapsidated rAAV vector away from components found in the biological system (most typically tissue culture) from which it was produced. Procedures for the purification of biological materials, including AAV vectors are well-known in the art, and may be found, e.g., in Sambrook and in Ausbel (both supra). Typically, AAV vectors (i.e., nucleic acids encapsidated in an AAV capsid) are purified by CsCl gradient or step gradient centrifugation (see, Sambrook). Typically, the vectors are approximately 90% pure after CsCl gradient centrifugation. Unpurified rAAV vectors (e.g., rAAV cell lysates) can also be used for cell transduction.

A "label" is a composition detectable by spectroscopic, photochemical, biochemical, immunochemical, or chemical means. For example, useful labels include 32P, fluorescent dyes, electron-dense reagents, enzymes (e.g., as commonly used in an ELISA), biotin, dioxigenin, or haptens and proteins for which antisera or Monoclonal antibodies are available.

A "labeled nucleic acid probe" is a nucleic acid probe that is bound, either covalently, through a linker, or through ionic, van der Waals or hydrogen bonds to a label such that the presence of the probe may be detected by detecting the presence of the label bound to the probe.

A "nucleic acid" is a deoxyribonucleotide or ribonucleotide polymer in either single- or double-stranded form, and unless otherwise limited, encompasses known analogs of natural nucleotides that function in a manner similar to naturally occurring nucleotides.

A "nucleic acid binding molecule" is a molecule with a high affinity for a nucleic acid. Such molecules include polycations, nucleic acid binding proteins, nucleic acids, antibodies, DNA intercalators (e.g., ethidium dimers), etc. The nucleic acid binding molecules of the present invention are typically coupled to a receptor ligand (e.g., an AAV helper virus or other receptor ligand such as transferrin), and serve to connect the receptor ligand to a nucleic acid (e.g., in one embodiment, the nucleic acid binding molecule is poly-1-lysine, which serves to connect transferrin to an AAV nucleic acid).

A "polycationic DNA binding domain" is a polycationic substance which binds to nucleic acids due to the strong affinity for the (anionic) nucleic acid caused by the polycationic charge. An example of a polycationic DNA binding domain is poly-1-lysine.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

A "promoter" is an array of nucleic acid control sequences which direct transcription of a nucleic acid. As used herein, a promoter includes necessary nucleic acid sequences near the start site of transcription, such as, in the case of a polymerase II type promoter, a TATA element. The promoter also includes distal enhancer or repressor elements which can be located as much as several thousand base pairs from the start site of transcription. A "constitutive" promoter is a promoter which is active under most environmental conditions and states of development or cell differentiation. An "inducible" promoter responds to an extracellular stimulus.

A "receptor-binding ligand" is a biological molecule which binds to a receptor molecule on the surface of a cell. The molecule is either naturally occurring or artificial (e.g., synthetic). Typically, in the context of the present invention, the binding of the receptor binding ligand to its cognate receptor results in endocytosis of the receptor binding ligand, along with materials which are attached to the receptor binding ligand.

The term "recombinant" when used with reference to a cell or virus indicates that the cell or virus encodes a nucleic acid whose origin is exogenous to the cell or virus type. Thus, for example, recombinant cells express genes that are not found within the native (non-recombinant) form of the cell.

A "recombinant expression cassette" is a nucleic acid construct, generated recombinantly or synthetically, with a series of specified nucleic acid elements which permit transcription of a particular nucleic acid. The recombinant expression cassette can be part of a plasmid, virus, or nucleic acid fragment. Typically, the recombinant expression cassette includes a nucleic acid to be transcribed, and a promoter. In some embodiments, the expression cassette also includes, e.g., an origin of replication, and/or chromosome integration elements.

A "recombinant encapsidatable adeno-associated virus nucleic acid" or rAAV nucleic acid refers to a nucleic acid which is generated, typically using genetic engineering techniques, from multiple nucleic acids. The rAAV nucleic acid has cis-active; sequences from the AAV viral genome which permit encapsidation of the nucleic acid into the AAV capsid, e.g., the ITR regions of AAV. An "encapsidatable" or "encapsulatable" rAAV nucleic acid has the cis-active nucleic acid sequences necessary packaging the nucleic acid into an AAV capsid (i.e., the AAV ITR regions). Typically, the rAAV nucleic acid is encapsidated in an AAV viral capsid to form an rAAV vector.

A "recombinant AAV helper nucleic acid" or more simply AAV helper nucleic acid is a nucleic acid which encodes functions which allow an AAV or rAAV nucleic acid to be encapsidated in an AAV capsid. Typically, in the context of the present invention, the helper plasmid, or other nucleic acid, encodes AAV functions and structural proteins which allow a recombinant AAV vector to be encapsidated into an AAV capsid. In one preferred embodiment, the recombinant AAV helper nucleic acid is a plasmid encoding AAV polypeptides, and lacking the AAV ITR regions. For example, in one embodiment, the helper plasmid encodes the AAV genome, with the exception of the AAV ITR regions, which are replaced with adenovirus ITR sequences. This permits replication and encapsidation of the AAV replication defective recombinant vector, while preventing generation of wild-type AAV virus, e.g., by recombination.

"Sequences necessary for AAV packaging" in the context of an AAV helper nucleic acid include AAV sequences active in trans found between or within the AAV ITR regions which encode nucleic acids and proteins necessary for encapsidation of the rAAV nucleic acid into an AAV capsid, e.g., typically the AAV capsid proteins (Vp1, Vp2, Vp3) and replicase proteins (Rep 78, Rep 68, Rep 40, Rep 52). In the context of the rAAV nucleic acid, "Sequences necessary for AAV packaging" refer to cis-active sequences which permit the rAAV nucleic acid to be "encapsidated" (packaged into an AAV viral capsid; "encapsulated" is equivalent terminology herein). These sequences typically include the AAV ITR regions.

A "target nucleic acid" is a nucleic acid to be used to transduce a cell. The target nucleic acid can integrate into a cell's genome, or remain episomal.

"Transfection" refers broadly to the process of causing a nucleic acid to enter a cell. In the art, the term is sometimes used to refer to a process wherein the nucleic acid is "naked," i.e., not in a viral capsid or associated with other biologicals. For purposes of the present invention "transfection" refers to the process of causing a nucleic acid to enter the cell as a "naked" nucleic acid, and/or to the process of causing a nucleic acid which is associated with other biologicals, such as nucleic acid binding molecules, helper viruses, receptor ligands etc. to enter a cell.

"Transduction" refers to the process in which a foreign nucleic acid (which is encapsidated in a viral capsid when outside of the cell) is introduced into a cell. The foreign nucleic acid is typically integrated into the cellular genome, but in some embodiments remains episomal.

"Titers" are numerical measures of the "concentration" of a virus or viral vector compared to a reference sample, where the concentration is determined either by the activity of the virus, or by measuring the number of viruses in a unit volume of buffer. The titer of viral stocks are determined, e.g., by measuring the infectivity of a solution or solutions (typically serial dilutions) of the viruses, e.g., on HeLa cells using the soft agar method (see, Graham & Van Der eb (1973) *Virology* 52:456–467) or by monitoring resistance conferred to cells, e.g., G418 resistance encoded by the virus or vector, or by quantitating the viruses by UV spectrophotometry (see, Chardonnet & Dales (1970) *Virology* 40:462–477).

"transferrin-poly-1-lysine" refers to the ligand for the transferrin receptor (transferrin) coupled (chemically or electrostatically to poly-1-lysine) is described, e.g., in Curiel (1991) *Proc. Natl. Acad Sci U.S.A.* 88:8850–8854 and Wagner et al. (1993) *Proc. Natl. Acad. Sci. U.S.A.* 89:6099–6013.

BRIEF DESCRIPTION OF THE DRAWINGS

FIG. 1 provides a schematic representation of the clone Rz2014. Shown are the AAV inverted terminal repeats (ITR), the intact MoMLV 5' LTR which controls the expression of the neomycin resistance gene (neo), the poly adenylation signal for neo (pA), the HIV U5 specific hairpin ribozyme (U5 Rz) under control of the valine tRNA pol III promoter (tRNAval), the truncated 3' MoMLV LTR and the 3' AAV ITR. Arrows indicate the direction of transcription. To construct this vector the retroviral vector pMJT (Yu et al. (1993) *Proc Natl Acad Sci U.S.A.* 90:6340–6344) was digested with XbaI and Sac II, gel purified, and then treated with T4 DNA polymerase to generate blunt ends. Subsequently, Xba 1 linkers were ligated to the blunt ended fragment followed by digestion with XbaI and gel purification to remove excess linkers. The XbaI pMJT fragment was then ligated to Xba 1 digested pSub201 (Samulski et al. (1987) *J Virol* 61:3096–3101).

DETAILED DESCRIPTION

AAV is a human parvovirus which requires a helper virus such as adenovirus or herpes virus to achieve productive infection. The virus can productively infect any cell within the host range of its helper virus, including human, simian, primate and rodent cells when the appropriate helper virus is used. In the absence of helper virus, infection of a cell with AAV results in integration of the AAV genome into the cell's genome. Cells infected with AAV show no adverse effects, or changes in morphology. AAV transduces a broad range of cells, including many which are not within the host range of AAV helper viruses (See, Samulski, supra) making it an ideal vector for transferring genes to a target cell. Until this invention, the primary problem with using AAV as a nucleic acid vector for the transduction of cells has been the difficulty in obtaining high titers of AAV-based vectors.

Curiel and co-workers have recently demonstrated that naked plasmid DNA bound electrostatically to poly-1-lysine or poly-1-lysine-transferrin which has been linked to defective adenovirus mutants can be delivered to cells with transfection efficiencies approaching 90% (Curiel et al. (1991) *Proc Natl Acad Sci U.S.A.* 88:8850–8854; Cotten et al. (1992) *Proc Natl Acad Sci U.S.A.* 89:6094–6098; Curiel et al. (1992) *Hum Gene Ther* 3:147–154; Wagner et al. (1992) *Proc Natl Acad Sci U.S.A.* 89:6099–6103; Michael et al. (1993) *J Biol Chem* 268:6866–6869; Curiel et al. (1992) *Am J Respir Cell Mol Biol* 6:247–252, and Harris et al. (1993) *Am J Respir Cell Mol Biol* 9:441–447). The adenovirus-poly-1-lysine-DNA conjugate binds to the normal adenovirus receptor and is subsequently internalized by receptor-mediated endocytosis. Herpes viruses have similar properties.

Our invention provides a system in which replication competent adenovirus added to a poly-1-lysine-DNA conjugate transfection system, delivers rAAV vector, AAV complementation vector, and adenovirus helper functions in a single transfection/infection step. In this invention, we describe the use of this and other procedures, and demonstrate that they result in a substantial and surprising increase in AAV vector transducing titer as compared to standard methods of rAAV vector production.

General Methods

Making Vectors, Nucleic Acids, Cell Culture and Antibodies

The practice of this invention involves the construction of nucleic acid vectors and the expression of genes in transfected cells. Molecular cloning techniques to achieve these ends are known in the art. A wide variety of cloning and in vitro amplification methods suitable for the construction of retroviral vectors are well-known to persons of skill. Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, N.Y., (Sambrook); and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel).

Examples of techniques sufficient to direct persons of skill through in vitro amplification methods, including the polymerase chain reaction (PCR) the ligase chain reaction (LCR), Qβ-replicase amplification and other RNA polymerase mediated techniques are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal Of NIH Research* (1991) 3, 81–94; (Kwoh et al. (1989) *Proc. Natl. Acad. Sci. U.S.A.* 86, 1173; Guatelli et al. (1990) *Proc. Natl. Acad. Sci. U.S.A.* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; and Barringer et al. (1990) *Gene* 89, 117. Improved methods of cloning in vitro amplified nucleic acids are described in Wallace et al., U.S. Pat. No. 5,426,039.

Oligonucleotide synthesis, useful in cloning or amplifying nucleic acids, is typically carried out on commercially available solid phase oligonucleotide synthesis machines (Needham-VanDevanter et al. (1984) *Nucleic Acids Res.* 12:6159–6168) or chemically synthesized using the solid phase phosphoramidite triester method described by Beaucage et. al. (Beaucage et. al. (1981) *Tetrahedron Letts.* 22 (20): 1859–1862).

Methods of transfecting and expressing genes in mammalian cells are known in the art. Transducing cells with viral vectors can involve, for example, incubating viruses with cells within the viral host range under conditions and concentrations necessary to cause infection. See, e.g., *Methods in Enzymology*, vol. 185, Academic Press, Inc., San Diego, Calif. (D. V. Goeddel, ed.) (1990) or M. Krieger, *Gene Transfer and Expression—A Laboratory Manual*, Stockton Press, New York, N.Y., (1990) and the references cited therein.

The culture of cells used in the present invention, including cell lines and cultured cells from tissue or blood samples is well known in the art. Freshney (*Culture of Animal Cells, a Manual of Basic Technique, third edition* Wiley-Liss, New York (1994)) and the references cited therein provides a general guide to the culture of cells.

Cell surface receptors are optionally bound by antibodies in one of the embodiments of the present invention. Methods of producing polyclonal and monoclonal antibodies are known to those of skill in the art. See, e.g., Coligan (1991) *Current Protocols in Immunology* Wiley/Greene, N.Y.; and Harlow and Lane (1989) *Antibodies: A Laboratory Manual* Cold Spring Harbor Press, N.Y.; Stites et al. (eds.) *Basic and*

*Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) Nature 256:495–497. Other suitable techniques for antibody preparation include selection of libraries of recombinant antibodies in phage or similar vectors. See, Huse et al. (1989) *Science* 246:1275–1281; and Ward, et al. (1989) *Nature* 341:544–546. Specific Monoclonal and polyclonal antibodies (as well as other cell surface ligands) will usually bind a cell surface receptor with a KD of at least about 0.1 mM, more usually at least about 1 µM, and most preferably at least about 0.1 µM or better.

AAV Vectors Containing Foreign Nucleic Acids

Carter et at., U.S. Pat. No. 4,797,368 describe many of the relevant design considerations for constructing recombinant AAV vectors. In brief, AAV is a single-stranded, replication-defective DNA virus with a 4.7 kilobase (kb) genome. AAV has palindromic inverted terminal repeats (ITRs, found at approximately nucleotides 1 to 145 at the left end of the wild-type AAV genome and 4681 to 4536 at the right end of the AAV genome) responsible for site-specific integration of wild-type AAV into a host chromosome (e.g., the q arm of human chromosome 19). The ITR regions are sufficient to permit packaging of a recombinant nucleic acid construct which is contained between the ITR regions, provided the missing AAV functional and structural elements are supplied in trans. Typically, AAV vectors include approximately 300 terminal nucleotides (the AAV ITRs) for packaging. For efficient packaging of an AAV vector to occur, the recombinant nucleic acid, including the ITR regions, should not exceed the overall size of the wild-type genome (approximately 4.7 kb). The ITR regions, in addition to providing packaging sequences, can also act as transcriptional promoters. Additional transcriptional promoters such as the AAV $p_5$ promoter (nucleotides 145 to 268 from AAV, see Carter WO 93/24641) are optionally included in the constructs.

Where the wild-type DNA regions between the ITRs are replaced with a heterologous nucleic acid, the missing functions are supplied in trans from a helper construct (e.g., an expression plasmid containing AAV coding sequences such as replicase and capsid proteins).

Making Nucleic Acid Binding Molecule/AAV/ helper Nucleic Acid/helper Virus Constructs Compositions for binding, e.g., AAV nucleic acids, AAV helper nucleic acids, or modified versions thereof are known. These compositions include polycations such as poly-1-lysine, polyarginine, polyornithine, as well as poly-heterologous cations such as positively charged polyaminoacids and non-peptide-based polycations such as polyethyleneimine. Naturally occurring or synthetic proteins which bind nucleic acids due to their polycationic charge, such as histones, protamines or analogues or fragments thereof are also appropriate nucleic acid binding molecules. Other suitable substances include intercalating agents such as ethidium dimers, acridine, and intercalating peptides containing tryptophan, tyrosine or phenylalanine.

Methods of complexing nucleic acids to a virus such as adenovirus using the above compositions are described, e.g., in Curiel et al. U.S. patent application Ser. No. 07/768,039. The present invention provides for the transduction of a cell with an AAV nucleic acid, helper nucleic acid and a helper virus which is a ligand of a cellular receptor, such as adenovirus or herpes virus, or modified version thereof. Other receptor ligands, including transferrin can also be bound to the above compositions (chemically, recombinantly, or electrostatically), facilitating endocytosis of the complex through a cellular receptor.

Receptor Ligand-Nucleic Acid Binding Conjugates

An efficient method of transfecting mammalian cells utilizes binding of a receptor ligand to a cell-surface receptor. Thousands of cell-surface receptor ligands are known in the art, including viruses such as HIV and adenovirus, sugars such as galactose, glucose, and mannose, immunoglobulins such as IgG, antibodies against surface receptors such as anti-CD4$^+$ or anti-CD$^+$7, polypeptides such as insulin or epidermal growth factor, glycopolypeptides such as transferrin or asialoglycoprotein, steroids such as cholesterol, and low density lipoproteins such as those containing apo-B. See, Darnell et al. (1990) *Molecular Cell Biology Second Edition* Scientific American Books New York for an introduction to receptor mediated endocytosis. The R&D systems 1995 source catalog for cytokines and related reagents (R&D systems 614 McKinley Place N.E. Minneapolis, Minn. 55413) and the references therein describe hundreds of receptors and ligands, including interleukins, antibodies, adhesion molecules, growth factors, cytokines and chemokines. Additional receptors and ligands are found in Pigott and Power (1993) *The Adhesion Molecule Facts Book* Academic Press Ltd. San Diego, Calif. and the references therein; Birch and Lennox (eds) (1995) *Monoclonal Antibodies Principles and Applications* Wiley-Liss New York; and in Paul, Sambrook, and Ausbel (all supra).

A. Binding Ligands and Nucleic Acid Binding Molecules

Cell surface receptor ligands and nucleic acid binding molecules are typically bound together chemically or, where the ligand and nucleic acid binding molecules are both polypeptides, are optionally synthesized recombinantly as a fusion protein. The procedure for attaching a nucleic acid binding molecule to a receptor ligand will vary according to the chemical structure of the nucleic acid binding molecule and the cell surface receptor ligand. Polypeptides typically contain variety of functional groups; e.g., carboxylic acid (COOH) or free amine (—NH$_2$) groups, which are available for reaction with a suitable functional group on either the ligand or the nucleic acid binding molecule where the ligand or the nucleic acid binding molecule is a polypeptide.

Alternatively, polypeptides are derivitized to attach additional reactive functional groups. The derivatization optionally involves attachment of linker molecules such as those available from Pierce Chemical Company, Rockford, Ill. A "linker", as used herein, is a molecule that is used to join the nucleic acid binding molecule to the receptor ligand. The linker is capable of forming covalent bonds to both the nucleic acid binding molecule and the ligand. Suitable linkers are well known to those of skill in the art and include, but are not limited to, straight or branched-chain carbon linkers, heterocyclic carbon linkers, or peptide linkers. Where the ligand and the nucleic acid binding molecule are polypeptides, the linkers are joined to the constituent amino acids through their side groups (e.g., through a disulfide linkage to cysteine) or to the alpha carbon amino and carboxyl groups of the terminal amino acids.

A bifunctional linker having one functional group reactive with a group on a particular ligand, and another group reactive with a nucleic acid binding molecule, can be used to form the desired conjugate. Alternatively, derivatization can proceed through chemical treatment of the ligand or nucleic acid binding molecule, e.g., glycol cleavage of the sugar moiety of a glycoprotein with periodate to generate free aldehyde groups. The free aldehyde groups on the glycoprotein may be reacted with free amine or hydrazine groups on an agent to bind the agent thereto (See, e.g., U.S. Pat. No. 4,671,958). Procedures for generation of free sulfhydryl groups on polypeptides are known (See, e.g., U.S. Pat. No. 4,659,839).

Many procedures and linker molecules for attachment of various compounds to proteins are known. See, for example, European Patent Application No. 188,256; U.S. Pat. Nos. 4,671,958, 4,659,839, 4,414,148, 4,699,784; 4,680,338; 4,569,789; and 4,589,071; and Borlinghaus et al. *Cancer Res.* 47: 4071–4075 (1987). In particular, production of various antibody conjugates is well-known within the art and can be found, for example in Thorpe et al., *Monoclonal Antibodies in Clinical Medicine,* Academic Press, pp. 168–190 (1982), Waldmann, *Science,* 252:1657 (1991), and U.S. Pat. Nos. 4,545,985 and 4,894,443.

A number of antibodies which bind cell surface receptors are known and have been converted to form suitable for incorporation into fusion proteins. These include anti-erbB2, anti-erbB3, BR96, OVB3, anti-transferrin, Mik-β1 and PR1 (see Batra et al., *Mol. Cell. Biol.,* 11:2200–2205 (1991); Batra et al., *Proc. Natl. Acad. Sci. U.S.A.,* 89:5867–5871 (1992); Brinkmann, et al. *Proc. Natl. Acad. Sci. U.S.A.,* 88:8616–8620 (1991); Brinkmann et at., *Proc. Natl. Acad. Sci. U.S.A.,* 90:547–551 (1993); Chaudhary et at., *Proc. Natl. Acad. Sci. U.S.A.,* 87:1066–1070 (1990); Friedman et al., *Cancer Res.* 53:334–339 (1993); Kreitman et al., *J. Immunol.,* 149:2810–2815 (1992); Nicholls et al., *J. Biol. Chem.,* 268:5302–5308 (1993); and Wells, et al., *Cancer Res.,* 52:6310–6317 (1992), respectively).

B. Production of Fusion Proteins

Where the cell surface receptor ligand and/or the nucleic acid binding molecule are relatively short polypeptides (i.e., less than about 50 amino acids) they are often synthesized using standard chemical peptide synthesis techniques. Where both molecules are relatively short, a chimeric molecule is optionally synthesized as a single contiguous polypeptide. Alternatively, the ligand and the nucleic acid binding molecule can be synthesized separately and then fused chemically. A ligand-nucleic acid binding molecule construct is referred to as a receptor-targeted fusion molecule.

Solid phase synthesis in which the C-terminal amino acid of the sequence is attached to an insoluble support followed by sequential addition of the remaining amino acids in the sequence is a preferred method for the chemical synthesis of the ligands of this invention. Techniques for solid phase synthesis are described by Barany and Merrifield, *Solid-Phase Peptide Synthesis;* pp. 3–284 in *The Peptides: Analysis, Synthesis, Biology. Vol. 2: Special Methods in Peptide Synthesis, Part A.,* Merrifield, et al. *J. Am. Chem. Soc.,* 85:2149–2156 (1963), and Stewart et al., *Solid Phase Peptide Synthesis,* 2nd ed. Pierce Chem. Co., Rockford, Ill. (1984) which are incorporated herein by reference.

In a preferred embodiment, the receptor-targeted fusion molecules of the invention are synthesized using recombinant nucleic acid methodology. Generally this involves creating a nucleic acid sequence that encodes the receptor-targeted fusion molecule, placing the nucleic acid in an expression cassette under the control of a particular promoter, expressing the protein in a host, isolating the expressed protein and, if required, renaturing the protein. Techniques sufficient to guide one of skill through such procedures are found in, e.g., Berger, Sambrook, Ausubel, Innis, Goeddel, Krieger, and Freshney (all supra).

While the two molecules are often joined directly together, one of skill will appreciate that the molecules are optionally separated by a peptide spacer consisting of one or more amino acids. Generally the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity.

Once expressed, recombinant fusion proteins are purified according to standard procedures, including ammonium sulfate precipitation, affinity columns, column chromatography, gel electrophoresis and the like (see, generally, R. Scopes, *Protein Purification,* Springer-Verlag, N.Y. (1982), Deutscher, *Methods in Enzymology Vol. 182: Guide to Protein Purification.,* Academic Press, Inc. N.Y. (1990)). Substantially pure compositions of about 50 to 95% homogeneity are preferred, and 80 to 95% or greater homogeneity are most preferred for use in the methods of the invention.

One of skill in the art will recognize that after chemical synthesis, biological expression, or purification, the receptor targeted fusion molecule may possess a conformation substantially different than the native conformations of the constituent polypeptides. In this case, it is often necessary to denature and reduce the polypeptide and then to cause the polypeptide to re-fold into the preferred conformation. Methods of reducing and denaturing proteins and inducing re-folding are well known to those of skill in the art (See, Debinski et al. (1993) *J. Biol. Chem.* 268:14065–14070; Kreitman and Pastan (1993) *Bioconjug. Chem.* 4: 581–585; and Buchner et al. (1992) *Anal. Biochem.,* 205:263–270.

C. Transferrin

The glycoprotein transferrin is a preferred cell surface ligand for the present invention, and is used in the Examples below for illustrative purposes; however, one of skill will recognize that a wide variety of cell surface ligands can be used in the practice of the invention. Binding of transferrin to its conjugate cell-surface receptor causes endocytosis of the receptor and transferrin into the cell. Molecules attached to transferrin are also endocytosed. Thus, AAV vectors, helper viruses, and rAAV helper plasmids are endocytosed if they are bound to transferrin and subsequently contacted with the transferrin receptor. Typically, the transferrin molecule is complexed with a nucleic acid binding molecule such as a polycation (e.g., poly-1-lysine) which binds nucleic acids, including rAAV nucleic acids and rAAV helper plasmids, e.g., through electrostatic interactions with the nucleic acid. Methods of generating polycationic-transferrin conjugates are found in U.S. patent application Ser. No. 07/768,039 (Curiel et al.); Wagner et al. (1990) *Proc. Natl. Acad. Sci. U.S.A.* 87:3410–3414; Wagner et al. (1991) *Proc. Natl. Acad. Sci. U.S.A.* 88:4255–4259; and EP-A1 0388 758.

An Increase In AAV Vector Titer Using Poly-1-lysine/adenovirus Cotransfection

Figure 1:
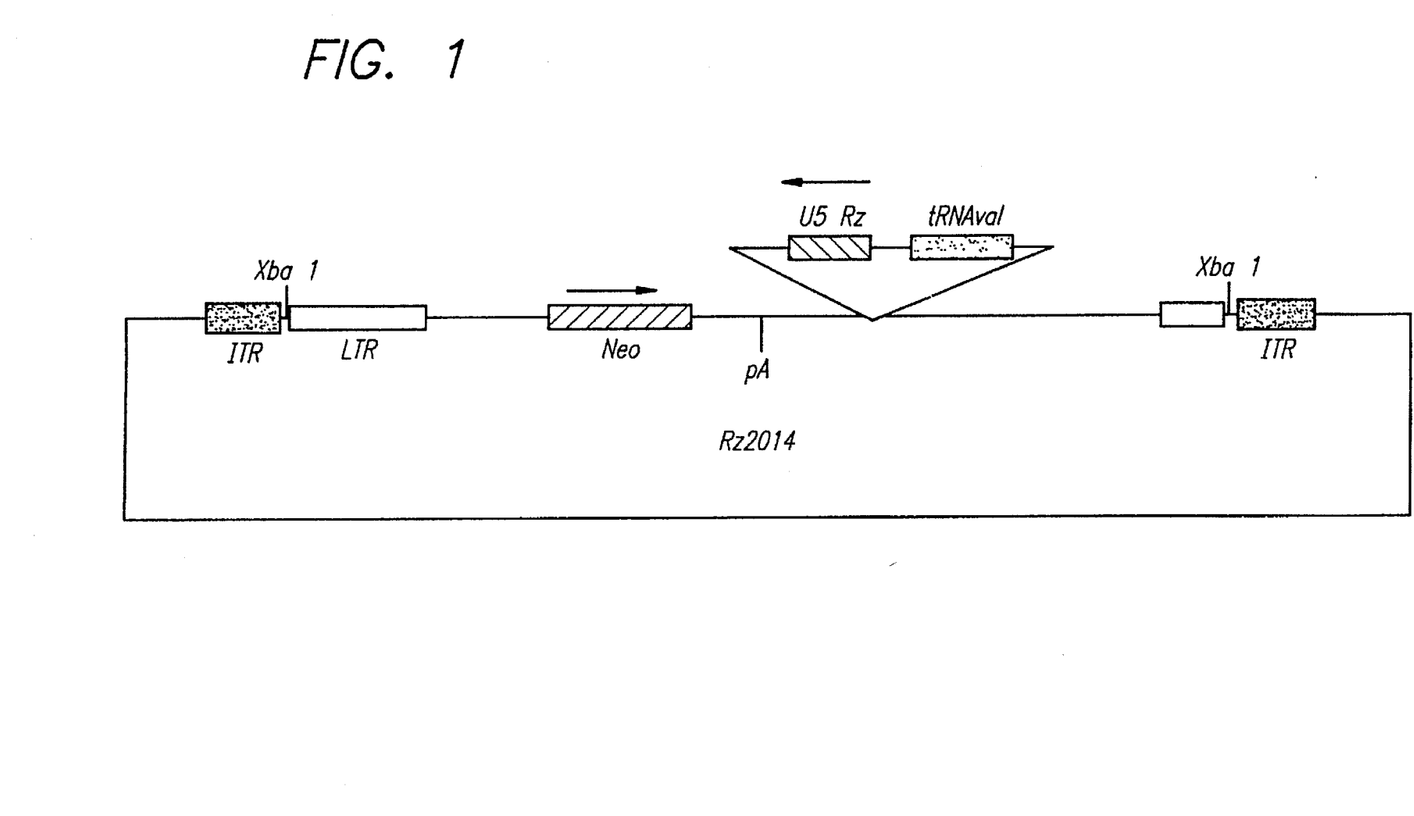

An infectious molecular clone of AAV (pSub201) (Samulski et al. (1987) *J Virol* 61:3096–3101) was used to generate an rAAV vector, Rz2014, which produces an HIV-1 leader sequence specific ribozyme (see, FIG. 1). Ad8 is an AAV substitution mutant which contains all of the wild type (WT) AAV coding sequences but has the AAV inverted terminal repeats (ITRs) replaced with adenovirus ITRs (Samulski et al. (1989) *J Virol* 63:3822–3828). This vector allows for efficient production of the AAV structural and regulatory proteins necessary for encapsidation, but contains no homology with the rAAV vector and therefore prevents the production of WT AAV virus during the packaging procedure.

We routinely obtained titers of $10^4$ transducing units/ml for the Rz2014 vector by standard calcium phosphate transfection (see, Sambrook). To make this determination, HeLa cells were plated at $1/20^{th}$ confluency and grown overnight. A dilution series of rAAV vector (containing a gene for G418 resistance) was added the following day. The cells were then selected on G418 the next day at 500 µg/ml. The cells were then grown for 10 days with fresh G418 being added every day. After 10 days visible colonies formed, and were counted for each dilution of the vector.

The results shown in Table 1 (see, Example 1 below) indicate a 44 fold increase in rAAV vector production when adenovirus-poly-1-lysine-nucleic acid conjugates were used as the method of transfection relative to calcium phosphate mediated transfection. This increase in titer was consistent between different batch preparations of adenovirus-poly-1-lysine conjugates, and is the result of rAAV particle formation. See, the examples below.

AAV Titer Shows Enhanced Temporal Effects When a Cell is Co-infected With AAV and Adenovirus The observed increase in rAAV titer is due in part to extremely efficient uptake of DNA through adenovirus receptor-mediated endocytosis. However, an additional mechanism also plays a role in this increase. We observed that when DNA was delivered by a replication incompetent adenovirus (Ad $dl_{1014}$) cross-linked to poly-1-lysine, a substantial increase in rAAV titer was obtained if the cells were infected with Ad5, a wild-type AAV on deposit with the ATCC (ATCC Vr-5), at the time of transfection instead of 4 hrs prior to transfection, as is usually done with calcium phosphate-mediated transfection. In the prior art, cells are typically pre-infected with adenovirus because the AAV transfection step interferes with the adenovirus infection process. Thus, the increase in rAAV titer by adenovirus-poly-1-lysine-DNA conjugates is not only a result of increased uptake of DNA, but also reflects an enhanced temporal interaction between AAV encapsidation processes and adenovirus helper functions, which is not possible with DNA transduction by standard calcium phosphate transduction methods.

Adenovirus Infection Through the Transferrin Receptor

Cross-linking of Ad5 to poly-1-lysine resulted in a significant decrease in the infectious titer of the virus (a drop from $2 \times 10^{10}$ PFU/ml to $3 \times 10^7$ PFU/ml after cross-linking). One explanation for the drop in viral infectivity is that random cross-linking of poly-1-lysine to virus particles interferes with receptor binding of a proportion of the virus particles.

To increase the overall infectivity of the cross-linked virus preparation, and thereby increase its transfection efficiency, we added transferrin-poly-1-lysine to the adenovirus-poly-1-lysine-DNA conjugate, so that the complexed adenovirus would now infect cells via the transferrin receptor. The results shown in Table 1 indicate a 6-fold increase in the resulting rAAV titer when poly-1-lysine-transferrin was used to form the adenovirus-DNA complex relative to poly-1-lysine. Thus, the total increase in transducing rAAV titer by delivery with adenovirus poly-1-lysine-transferrin DNA complexes relative to calcium phosphate mediated transfection was 245 fold.

The results presented herein show that the efficient DNA delivery techniques of the invention yield significantly higher rAAV titers than what is typically achieved by conventional methods of transfection. If this procedure is coupled to a purification scheme which allows for concentration of large scale preparations of recombinant virus, then very high transducing titers of rAAV are easily produced.

Utility of AAV Vectors

AAV vectors stably transduce cells with nucleic acids of interest. Accordingly, the vectors have a variety of in vitro utilities. Essentially any polypeptide or nucleic acid which is encoded by a nucleic acid smaller than 4.7 kb can be stably produced in a mammalian cell of choice. Thus peptide therapeutics (e.g., insulin, or epidermal growth factor) are produced from cells transduced with an appropriate vital vector. Similarly, diagnostic peptides such as viral peptides used in commercial ELISA assays (e.g., HIV peptides) are stably produced from cells transfected with the vectors of the invention. Nucleic acids are also produced using the vectors of the invention, useful, e.g., as probes or therapeutic agents.

AAV vectors are particularly useful in gene therapeutic applications, due to their ability to stably transduce a broad array of cell types, in both dividing and non-dividing states.

A. Ex Vivo Therapy

Methods for inhibiting viral replication in a cell in an organism involve transducing the cell ex vivo with a vector of this invention, and introducing the cell into the organism. The choice of cell target depends upon the disease to be treated. For instance, in the case of HIV treatment, T cells are targeted for transduction by the vectors of the invention (e.g., with anti-HIV nucleic acids; see, Wong Staal et al. copending application Ser. No. 08/442,061). For example, where the vectors are used in gene therapy protocols for the treatment of HIV infection, hematopoietic stem cells, which are derived from bone marrow or fetal cord blood or T-lymphocytes or monocytes (e.g., cultured from a patient) would be transduced. Similarly, where the disease to be treated is hepatitis, hepatocytes would be transduced. The cells can be from an individual or stored cells in a cell bank (e.g., a blood bank).

B. In Vivo Therapy

The vectors of the invention can be administered directly to the patient for transduction of cells in vivo. Administration can be by any of the routes normally used for introducing virus into contact with blood or tissue cells. The vectors of the present invention can be used e.g., to treat or prevent cancers, enzyme deficiencies, and virally-mediated diseases such as AIDS in patients. The vectors used in the present inventive method are administered in any suitable manner, preferably with pharmaceutically acceptable carriers. Suitable methods of administering such vectors in the context of the present invention to a patient are available, and, although more than one route can be used to administer a particular vector, a particular route often provides a more immediate and more effective reaction than another route.

Pharmaceutically acceptable carriers are determined in part by the particular vector being administered, as well as by the particular method used to administer the composition. Accordingly, there is a wide variety of suitable formulations of the pharmaceutical compositions of the present invention.

Formulations suitable for oral administration can consist of (a) liquid solutions, such as an effective amount of the vector dissolved in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art.

The vector, alone or in combination with other suitable components, can be made into aerosol formulations to be administered via inhalation. Because the bronchial passageways are the usual route of choice for certain viruses, corresponding vectors are appropriately administered by this method. Aerosol formulations can be placed into pressurized acceptable propellants, such as dichlorodifluoromethane, propane, nitrogen, and the like.

Suitable formulations for rectal administration include, for example, suppositories, which consist of the active vector with a suppository base. Suitable suppository bases include natural or synthetic triglycerides or paraffin hydrocarbons. In addition, it is also possible to use gelatin rectal capsules which consist of a combination of the vector with a base, including, for example, liquid triglyercides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and in some embodiments, can be stored in a freeze-dried (lyophilized) condition requiring only the addition of the sterile liquid carrier, for example, water, for injections, immediately prior to use. For many vectors, this mode of administration will be appropriate, because AAV virions are not typically destroyed by lyophilization. Extemporaneous injection solutions and suspensions can be prepared from sterile powders, granules, and tablets of the kind previously described. Cells transduced by the vector as described above in the context of ex vivo therapy can also be administered parenterally as described above, except that lyophilization is not generally appropriate, since cells are destroyed by lyophilization.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector or transduced cell type in a particular patient.

In determining the effective amount of the vector to be administered in the treatment or prophylaxis of virally-mediated diseases such as AIDS, the physician needs to evaluate circulating plasma levels, vector toxicities, and profession of the disease.

In the practice of this invention, the vectors can be administered, for example, by intravenous infusion, orally, topically, intraperitoneally, intravesically or intrathecally. The preferred method of administration will often be oral, rectal or intravenous, but the vectors can be applied in a suitable vehicle for the local and topical treatment of virally-mediated conditions.

The vectors of this invention can supplement treatment of diseases by any known conventional therapy, including cytotoxic agents, nucleotide analogues and biologic response modifiers.

For administration, vectors and transduced cell types of the present invention can be administered at a rate determined by the LD-50 of the vector, and the side-effects of the vector or cell type at various concentrations, as applied to the mass and overall health of the patient. Administration can be accomplished via single or divided doses.

EXAMPLES

The following examples are provided by way of illustration only and not by way of limitation. Those of skill will readily recognize a variety of noncritical parameters which could be changed or modified to yield essentially similar results.

Example 1

High Titer AAV Vectors

One of the principal problems with using recombinant adeno-associated virus vectors (rAAV) as vehicles for gene delivery has been the difficulty in obtaining high titer virus stocks after the initial transfection into producer cells. In this example we describe a method for transfecting cells at extremely high efficiency with rAAV vector DNA and complementation plasmid while simultaneously infecting those cells with replication competent adenovirus using adenovirus poly-1-lysine DNA complexes. We further show that this technique results in an increase in rAAV transducing titer by two orders of magnitude over what is typically achieved by standard calcium phosphate transfection.

Figure 2:
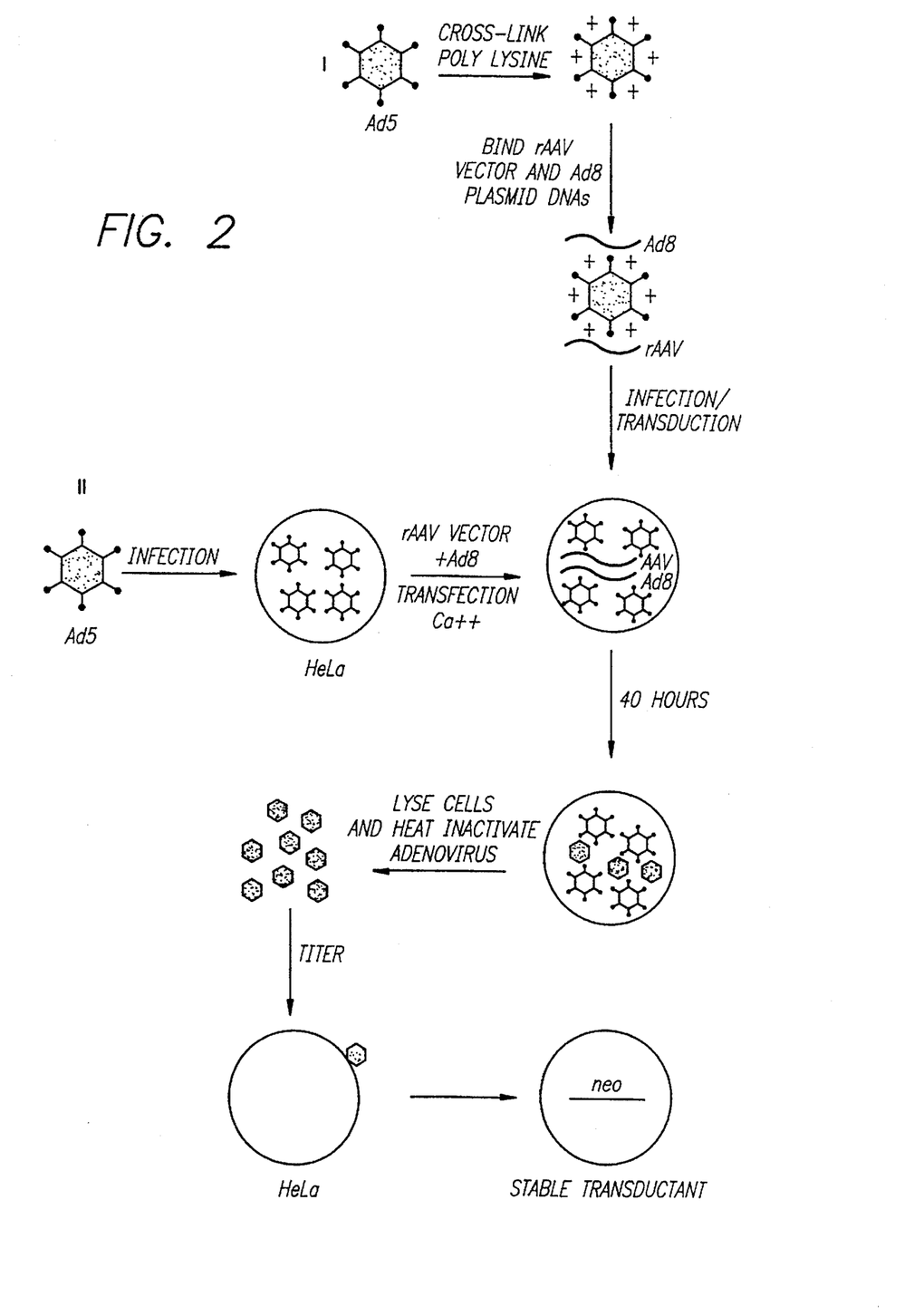
FIG. 2 provides a schematic representation of (I) DNA delivery by adenovirus-poly-1-lysine DNA conjugates vs. calcium phosphate mediated transfection (II).

Cesium chloride purified adenovirus was cross-linked to poly-1-lysine with EDC and this preparation was subsequently used to bind plasmid DNAs Rz2014 and Ad8 as described below and as depicted in FIG. 2. WT adenovirus type 5 (ADS, ATCC VR-5) was grown in HeLa cells and then banded two times on CsCl step gradients of 1.33 and 1.45 g/ml CsCl. Following purification the CsCl was removed by elution with 2 ml 5 mM HEPES, pH 7.8; 150 mM NaCl (HBS) in a PD10 gel filtration column (Pharmacia). The eluate was then brought up to a final volume of 3.6 ml with HBS and either used for cross-linking or diluted 1:5 with 10 mM Tris, pH 8.0; 100 mM NaCl; 1 mg/ml BSA; and 50% glycerol and frozen at −70° C. for future use. Virus stocks were titrated on HeLa cells using the soft agar method as previously described (Graham & Van Der eb (1973) *Virology* 52:456–467) or quantitated by UV spectrophotometry (Chardonnet & Dales (1970) *Virology* 40:462–477). Linkage of poly-L-lysine to Ad5 was performed with the cross-linking agent 1-ethyl-3-(3-dimethylaminopropyl)carbodiimide hydrochloride (EDC) as previously described (Cristiano et al. (1993) *Proc Natl Acad Sci* 90, 11548–11552).

For production of rAAV particles, 100 µl of poly-1-lysine cross-linked Ad5 or Ad $dl_{1014}$ was mixed with 5 µg of CsCl purified rAAV plasmid DNA (Rz2014) and 5 µg of Ad8 plasmid DNA in 100 µl of 20 mM HEPES, pH 7.3, 150 mM NaCl. After 30 min at room temperature, 4 µl of 1 mg/ml poly-1-lysine or 6 µl of transferrin-polyl-1-lysine was mixed with 100 µl or 200 µl of 20 mM HEPES, pH 7.3; 150 mM NaCl, respectively, and then added to the reaction. The reaction was then incubated for an additional 30 min at room temperature and then mixed with 5 ml of DMEM plus 2% FCS and added to HeLa cells which were previously grown to 80% confluence in a 75 cm² flask. The cells were then incubated for 1 hour at 37° C. and 5 ml of DMEM plus 18% FCS was added.

Calcium phosphate-mediated transfection was as described (see, Sambrook) using 5 µg of Rz2014 DNA and 5 µg of Ad8 DNA on 80% confluent HeLa cells which had been infected 4 hrs previous with Ad5 at an MOI of 5–10. Approximately 40 hrs post-transfection, either by adenovirus poly-1-lysine-DNA complexes or by calcium phosphate, maximum CPE was observed and the cells were dislodged by gentle tapping or scrapping into the culture supernatant. The cells were then harvested by centrifugation at 500×g at 4° C. and then resuspended in 0.5 ml of RPMI1640 medium plus 10% FCS. The cells were then lysed by 3 cycles of freeze/thaw and cell debris were removed by centrifugation at 2000 g at 4° C. Adenovirus in the lysate was inactivated by heating at 56° C. for 30 min and aliquots of the lysate were then stored at −70° C. for future use. Titration of the lysate was on HeLa cells by selection for G418 resistance using standard techniques. See, Freshney et al. (Supra) for a description of plating mammalian cells. Briefly, HeLa cells were plated at $\frac{1}{20}^{th}$ confluency and grown overnight. A dilution series of rAAV vector (containing a gene for G418 resistance) was added the following day. The cells were then selected on G418 the next day at 500 µg/ml. The cells were then grown for 10 days with fresh G418 being added every day. After 10 days visible colonies formed. Counting colonies for the various dilutions provides a standard measure of rAAV vector titer.

Following formation of the adenovirus-poly-1-lysine-DNA conjugate, the material was added to HeLa cells that were approximately 80% confluent. In parallel, Rz2014 and Ad8 DNAs were used to form a calcium phosphate co-precipitate which was then added to 80% confluent HeLa cultures that had been infected at a multiplicity of infection (MOI) of 5–10 with Ad5 4 hrs earlier. The following day the medium was changed in the HeLa cultures that were treated with calcium phosphate precipitated DNA, but not in the cultures treated with adenovirus-poly-1-lysine-DNA conjugate, as no profound deleterious effect on the cells was observed by the adenovirus-mediated transfection.

The next day (40 hrs post-transfection), typical adenovirus cytopathic effect was observed in both cultures. The cells in each of these cultures were harvested and lysed by freeze/thaw and the transducing rAAV titer was determined by selection for G418 resistance. We routinely obtained titers of $10^4$ transducing units/ml for the Rz2014 vector by standard calcium phosphate transfection. Although other investigators have reported higher rAAV titers, the observed high transfection rates are vector dependent, and not due to inconsistencies in transfection efficiency (Muzyczka (1992) *Curr Top in Microbiol and Immunol* 58:97–129). In contrast, the results shown in Table 1 indicate a 44 fold increase in rAAV vector production when adenovirus-poly-1-lysine DNA conjugates were used as the method of transfection relative to calcium phosphate mediated transfection. This increase in titer was consistent between different batch preparations of adenovirus-poly-1-lysine conjugates and is the result of rAAV particle formation, since exclusion of the complementation plasmid (AD8) yielded no G418 resistant colonies.

The observed increase in rAAV titer is due to extremely efficient uptake of DNA through adenovirus receptor-mediated endocytosis. However, an additional mechanism plays a role in this increase as well. We observed that when DNA was delivered by a replication incompetent adenovirus (Ad $dl_{1014}$) cross-linked to poly-1-lysine, a substantial increase in rAAV titer was obtained if the cells were infected with Ad5 at the time of transfection instead of 4 hrs prior to transfection, as is usually done with calcium phosphate-mediated transfection because the transfection step interferes with the adenovirus infection process (Chatterjee & Wong (1993) *Methods: A Companion to Methods in Enzymology* 5:51–59) (see, Table 1 for the results of the two procedures). Thus, the increase in rAAV titer by adenovirus-poly-1-lysine-DNA conjugates is not only a result of increased uptake of DNA, but also reflects an enhanced temporal interaction between the AAV encapsidation processes and adenovirus helper functions, in contrast to DNA transfection by the calcium phosphate method.

Cross-linking of Ad5 adenovirus to poly-1-lysine resulted in a significant decrease in the infectious titer of the virus (a drop from $2 \times 10^{10}$ PFU/ml to $3 \times 10^7$ PFU/ml after cross-linking). To determine whether random cross-linking of poly-1-lysine to virus particles interferes with receptor binding of a proportion of the virus particles causing the drop in infectivity we added transferrin-poly-1-lysine to the adenovirus-poly-1-lysine-DNA conjugate, so that the complexed adenovirus would infect cells via the transferrin receptor (Curiel et al. *Hum Gene Ther* 3:147–154). The results shown in Table 1 indicate a 6 fold increase in the resulting rAAV liter when poly-lysine-transferrin was used to form the adenovirus-DNA complex relative to poly-1-lysine. Thus, the total increase in transducing rAAV titer by delivery with adenovirus poly-1-lysine-transferrin DNA complexes relative to calcium phosphate mediated transfection was 245 fold.

The above results show that efficient DNA delivery yields significantly higher rAAV titers than what is typically achieved by conventional methods of transfection. When this procedure is coupled to a purification scheme which allows for concentration of large scale preparations of recombinant virus, very high transducing titers of rAAV are readily attainable. This invention, therefore, overcomes a major impediment to the use of AAV vectors.

TABLE 1

Comparison of rAAV titer obtained by calcium phosphate mediated transfections vs. adenovirus-poly-1-lysine-DNA conjugates.

| Method | #G418 resitant colonies | Fold[d] |
|---|---|---|
| Ca[++] | $1.1 \pm 0.5 \times 10^4$ | 1.00 |
| Ad(dl$_{1014}$)P1-DNA + Ad5(4 hrs)[a,c] | $5.4 \pm 0.6 \times 10^4$ | 4.90 |
| Ad(dl$_{1014}$)P1-DNA + Ad5[b,c] | $1.8 \pm 0.2 \times 10^5$ | 16.3 |
| Ad5P1-DNA[c] | $4.4 \pm 0.5 \times 10^5$ | 40.0 |
| Ad5-P1DNA-Tf[c] | $2.7 \pm 1.0 \times 10^6$ | 245 |
| Ad5P1-DNA[e] | $5.0 \pm 2.2 \times 10^5$ | — |
| Ad5P1-DNA without Ad8[e] | 0 | — |

[a]Ad5 added 4 hrs before transfection
[b]Ad5 added at time of transfection
[c]Values represent three independent transfections obtained from the same preparation (batch #1) of Ad5P1 or Ad(dl$_{1014}$)P1(P1 is an abbreviation for poly-1-lysine.
[d]Calculated as the number of G418 resistant colonies obtained under the indicated condition divided by the number of G418 resistant colonies obtained by calcium phosphate-mediated transfection.
[e]Values represent three independent transfections obtained from the same preparation (batch #2) of Ad5P1.

All publications and patent applications cited in this specification are herein incorporated by reference in their entirety for all purposes as if each individual publication or patent application were specifically and individually indicated to be incorporated by reference.

Although the invention has been described with reference to the presently-preferred embodiments, it should be understood that various modifications can be made without departing from the spirit of the invention. Accordingly, the invention is limited only by the claims that follow.

What is claimed is:

1. A method for producing high titers of recombinant adeno-associated virus (AAV) vector comprising the steps of:
   (i) binding a recombinant encapsidatable rAAV nucleic acid and a recombinant AAV helper nucleic acid, wherein the AAV helper nucleic acid comprises sequences necessary for rAAV replication and encapsidation, to an AAV helper virus, thereby producing a bound AAV helper virus;
   (ii) contacting a cell with the bound AAV helper virus; and
   (iii) culturing the cell under conditions which permit replication and encapsidation of the rAAV nucleic acid, thereby producing an rAAV vector.

2. The method of claim 1, wherein the AAV helper virus is an adenovirus.

3. The method of claim 1, wherein the AAV helper nucleic acid is replication defective.

4. The method of claim 1, wherein the AAV helper nucleic acid comprises adenovirus ITR sequences and AAV sequences.

5. The method of claim 1, wherein the AAV helper nucleic acid is Ad8.

6. The method of claim 1, wherein the AAV helper virus is replication defective.

7. The method of claim 1, wherein the cell is a human cell.

8. The method of claim 1, wherein step (ii) further comprises simultaneously infecting the cell with an adenovirus.

9. The method of claim 1, wherein the rAAV nucleic acid comprises AAV ITR sequences and heterologous nucleic acid sequences.

10. The method of claim 1, wherein the rAAV nucleic acid comprises AAV ITR sequences and heterologous anti-HIV nucleic acid sequences.

11. The method of claim 1, wherein the rAAV nucleic acid comprises AAV ITR sequences and heterologous anti-HIV ribozyme nucleic acid sequences.

12. The method of claim 1, wherein the method further includes the step of isolating the recombinant rAAV vector.

13. The method of claim 1, wherein the bound AAV helper virus of step (i) further comprises a nucleic acid binding molecule.

14. The method of claim 1, wherein the bound AAV helper virus of step (i) further comprises poly-1-lysine and transferrin-poly-1-lysine.

15. The method of claim 1, wherein the rAAV nucleic acid and the AAV helper nucleic acid are not homologous.

16. The method of claim 13, wherein the nucleic acid binding molecule is a polycation.

17. The method of claim 13, wherein the nucleic acid binding molecule is poly-1-lysine.

18. A method of replicating an rAAV vector through receptor mediated endocytosis, comprising:
   (i) binding an rAAV nucleic acid and an AAV helper nucleic acid to a receptor-binding ligand, thereby forming an AAV nucleic acid-receptor binding ligand complex, wherein the receptor-binding ligand, upon binding a cell membrane receptor causes endocytosis of the receptor and the receptor binding ligand;
   (ii) contacting a cell with the rAAV nucleic acid-AAV helper nucleic acid-receptor binding ligand complex; and,
   (iii) incubating the cell under conditions which permit replication and encapsidation of the rAAV nucleic acid, thereby creating an rAAV vector.

19. The method of claim 18, wherein the receptor binding ligand is an AAV helper virus.

20. The method of claim 18, wherein the receptor binding ligand is selected from the group consisting of adenovirus and herpes virus.

21. The method of claim 18, wherein the AAV nucleic acid-receptor binding ligand complex further comprises an AAV helper virus.

22. The method of claim 18, wherein the cell of step (ii) is infected with an AAV helper virus.

23. The method of claim 18, wherein the cell of step (ii) is infected with an AAV helper virus at the same time as it is contacted with the rAAV nucleic acid-AAV helper nucleic acid-receptor binding ligand complex of step (i).

24. A method of transducing a cell with a target nucleic acid, comprising:
   (i) binding a recombinant rAAV nucleic acid and a recombinant AAV helper nucleic acid to an AAV helper virus, thereby producing a bound AAV helper virus, wherein the AAV helper nucleic acid comprises sequences necessary for rAAV replication and encapsidation, and the rAAV nucleic acid comprises a target nucleic acid sequence;
   (ii) contacting a cell with the bound helper virus; and
   (iii) culturing the cell under conditions which permit replication and encapsidation of the rAAV nucleic acid, thereby producing an rAAV vector;
   (iv) isolating the rAAV vector, thereby producing an isolated rAAV vector; and
   (v) contacting a cell with the isolated rAAV vector, thereby transducing the cell.

25. The method of claim 24, wherein the cell is a human cell.

26. The method of claim 24, wherein the rAAV helper virus is an adenovirus.

27. A composition, comprising an AAV helper virus, nucleic acid binding molecule, rAAV nucleic acid and an AAV helper nucleic acid.

28. The composition of claim 27, further comprising transferrin.

29. The composition of claim 27, wherein the nucleic acid binding molecule is poly-1-lysine.

30. The composition of claim 27, wherein the AAV helper virus is an adenovirus.

* * * * *